United States Patent [19]

Eydelman et al.

[11] Patent Number: 5,206,671
[45] Date of Patent: Apr. 27, 1993

[54] TESTING AND TREATING OF VISUAL DYSFUNCTIONS

[76] Inventors: Malvina B. Eydelman, 368 Longwood Ave., Apt. 45, Boston, Mass. 02215; Shirley H. Wray, 987 Memorial Dr., Cambridge, Mass. 02138

[21] Appl. No.: 546,544
[22] Filed: Jun. 29, 1990
[51] Int. Cl.$^5$ ............................................. A61B 3/00
[52] U.S. Cl. .................................. 351/203; 351/223; 351/246
[58] Field of Search ............... 351/200, 201, 203, 223, 351/243, 246

[56] References Cited

U.S. PATENT DOCUMENTS

| | | |
|---|---|---|
| 3,545,847 | 12/1970 | Pietrini . |
| 3,891,311 | 6/1975 | Fletcher et al. . |
| 4,314,281 | 2/1982 | Wiggins et al. . |
| 4,348,186 | 9/1982 | Harvey et al. . |
| 4,402,580 | 9/1983 | Ross . |
| 4,550,990 | 11/1985 | Trispel et al. ........................ 351/222 |
| 4,634,243 | 1/1987 | Massof et al. . |
| 4,714,330 | 12/1987 | Hennequin . |
| 4,726,672 | 2/1988 | O'Brien et al. ........................ 351/203 |
| 4,756,305 | 7/1988 | Mateik et al. . |
| 4,861,154 | 8/1989 | Sherwin et al. . |
| 4,861,156 | 8/1989 | Terry . |
| 4,896,959 | 1/1990 | O'Brien . |

OTHER PUBLICATIONS

American Institute for Research, "Video Visual Skills User's Guide," Dec. 1986.
American Institute for Research, "TurboScan: A Special Reading Program," Dec. 1986.
Srebro, "Effect of Viewing High Luminance Gratings on the Amblyopic Visual System", 1984, British J. Ophthalmol., vol. 68, pp. 443-446.
Garzia, "Efficacy of Vision Therapy in Amblyopia: A Literature Review", 1987, Amer. J. Optometry & Physiological Optics, vol. 64, No. 6, pp. 393-404.
Fricker, et al., "Use of a Video-Game/Stripe Presentation for Amblyopia Therapy", Mar./Apr. 1981, J. Pediatric Opthalmol. & Strabismus, vol. 18, No. 2, pp. 11-16.

Primary Examiner—Rodney B. Bovernick
Assistant Examiner—Hung Xuan Dang

[57] ABSTRACT

A method for testing and treating visual dysfunctions (for example amblyopia) includes steps of providing an interactive visual game that presents to the patient a visual task, the visual game employing images scaled to the threshold visual parameter or parameters of the patient, and presenting a nonvisual reward to the patient for successful completion of the task. Also, apparatus for treating visual dysfunctions in a patient includes means for presenting an image to the patient, the image presenting a visual task to the patient, means for scaling the image to about the patient's threshold value for a visual parameter or parameters, means for providing an interaction between the patient and the image, and means for providing a reward for successful completion of the task. Also, an interactive video apparatus includes video display means for simultaneously stimulating a subject's interest and stimulating the subject's vision at about the maximum value of a visual parameter or parameters of which the subject is capable, means for receiving input from the subject, and means for providing to the subject a nonvisual reward for subject input that is appropriate to an image presented to the subject on the video display means. Also, a computerized method for testing a visual parameter or parameters comprises providing an interactive visual test that presents to the patient an image to be identified and, in step increments of increasing difficulty of the parameter in question, determining that patient's threshold value for the visual parameter or parameters by providing for interaction between the patient and the image.

8 Claims, 1 Drawing Sheet

TESTING AND TREATING OF VISUAL DYSFUNCTIONS

BACKGROUND OF THE INVENTION

This invention relates to testing for and treating defects in vision, and particularly to treating amblyopia.

Amblyopia is a defect in visual acuity of an eye that persists after refractive error in the eye has been corrected and any pathological obstacle to vision has removed. It is a leading cause of impaired visual acuity in one eye, affecting about 2% of persons in the U.S. Unless successfully treated, amblyopia constitutes a potential handicap.

A variety of approaches to treating amblyopia have been tried. Approaches based promoting the use of the amblyopic eye include, for example, optical penalization, administration of cycloplegic drugs, CAM visual stimulation and occlusion of the better eye.

Generally, in optical penalization, lenses are used to blur the visual acuity of the better eye and to aid the visual acuity of the amblyopic eye. Cycloplegic drugs (such as atropine) are administered to blur the vision of the better eye by preventing accommodation and decreasing the depth of focus. Such drugs must be used with caution, however; in particular, the defocused image resulting from the use of atropine is sufficient to produce stimulus deprivation amblyopia, and the atropine administration can result in light sensitivity and dissociation.

In one known approach, a near-vision fixation distance is found where the visual axes cross in convergent squint, and the patient's perception of this physiological diplopia is used to encourage the use of binocular vision. This brings the amblyopic eye into use with the other eye at one fixation distance, and results in an improvement in acuity. This method requires a high degree of interest and co-operation in the patient.

In an occlusion therapy known as Red filter occlusion, the amblyopic eye is occluded for most of each day except for a short period, increasing to half a day, during which the better eye is occluded and a dark red filter (Wratten filter No. 92) is placed before the amblyopic eye. With the red filter in place over the amblyopic eye and the occluder in place over the better eye, the patient is encouraged to use the amblyopic eye as much as possible. Evidence from clinical evaluations of this method is very conflicting, and the underlying theory behind it is doubtful.

In another general approach, a central after-image is created in the dominant eye, and transferred to the amblyopic eye. The patient is then asked to try to locate the after-image at the point of fixation, and to see smaller fixation letters. The procedure is repeated when the after-image fades, and the acuity is measured after several repeats. It appears that the best results are obtained when the starting acuity is 6/24 or better, and in those cases when the binocular vision and acuity has deteriorated following previous improvement achieved by other orthoptic procedures.

In one known approach, a special ophthalmoscope (termed "euthyscope") is used to center a wide ring after-image on the fovea of the amblyopic eye. The fovea itself is spared the after-image, while the surrounding retina, including the eccentrically fixing area, is desensitized by the after-image. The patient is then asked to look at individual letters in decreasing sizes with true foveal fixation. This method requires a substantial amount of practitioner's time, and is tiring for the patient, and to be effective, it must be rigorously applied. For these reasons this method has never gained wide acceptance.

In another approach, central fixation of the amblyopic eye is encouraged by asking the patient to see Haidinger's brushes. Initially, an empty bright blue field of rotating polarized light is used, and then a fixation letter or other target is introduced.

Occlusion of the non-amblyopic eye, 'direct occlusion', is a long established method and has proved to produce good results in many cases. The usual method is total occlusion, in which an attempt is made to ensure that no light enters the eye and the amblyopic eye is brought into use. Schedules for occlusion vary widely among practitioners, but generally, where total direct occlusion is thought to be the best procedure, the occlusion is maintained throughout the day, or at least during waking hours, for several months for a maximum response. Checks of the acuity of both eyes generally are carried out weekly throughout the treatment period, and according to one general rule of thumb no more than 1 week of constant patching for every year of the patient's age should be permitted between examinations. Although occlusion is sometimes necessary, it is not in all cases the preferred method. Where good binocular vision is the ultimate aim, covering one eye may not be the best way to start, since occlusion promotes monocular use.

Occlusion of the dominant eye is not entirely successful as a cure for amblyopia, not least because it is difficult to marshall full cooperation by patients and their families. The patient, typically a child or young adult, is asked to participate in daily activities, including school, with greatly reduced visual function. Patients often are embarrassed by their appearance while wearing the patch and are teased by their peers, and some patients suffer from skin irritation or allergic reactions to contact with the patch material. Moreover, there is in occlusion treatments a sense of being greatly removed from the source of therapy; the patients and their parents lose touch with the therapist and are not given the frequently necessary reinforcement and encouragement. Any of these factors can lead to distress and a decision not to continue with treatment, or to noncooperation by the patient.

Some of the problems encountered in total occlusion therapy can be alleviated by reducing the duration of each day's period of occlusion. Minimal occlusion therapy requires the child to wear a totally opaque patch for only 20 to 30 minutes a day, during which time the child plays some kind of visually demanding game. It is important with this form of therapy that the child concentrate hard on the task and that the task be as fine and difficult as the child is able to undertake.

An apparatus known as the "CAM visual stimulator" was devised to treat amblyopia by using intense visual stimulation of the amblyopic eye for short periods of time. In this therapeutic approach, occlusion is used during treatments but not at other times. The apparatus consists of a base on which is fitted one of six circular high contrast gratings, each of a different spatial frequency. The grating has a transparent cover on which the patient is encouraged to draw or to play drawing games to ensure that he concentrates on the grating. The patient draws on the transparent cover while the better eye is occluded and the grating beneath the cover is slowly rotated.

SUMMARY OF THE INVENTION

We believe that success in treatment of a patient for amblyopia can be achieved by providing an interactive visual game that presents a set of visual tasks, using as visual images cartoon characters scaled to the threshold visual acuity for that particular patient, and presenting a pleasing auditory reward to the patient for successful completion of a task.

Apparently the rotating grating pattern itself in the CAM visual stimulation approaches described above is not responsible or contributes little to the cited effects of the treatment. In some studies, subjects in a control group who used the apparatus with a uniform gray pattern in place of the rotating gratings showed as great improvements in acuity as those in experimental groups. It appears, rather, that where significant improvements in visual acuity are produced, the very brief periods of occlusion in combination with the highly demanding visual-motor tasks performed simultaneously are probably responsible.

According to the invention, a computerized system is provided which, during minimal occlusion therapy, presents a highly demanding visual task tailored to the particular patient's need. The invention provides the necessary motivation and attentiveness in the subject, by providing a visual stimulus or a series of visual stimuli selected to be interesting to the particular patient and to hold the particular patient's interest throughout the treatment session, and by providing to the patient an auditory reward chosen by the patient for correct performance of visually presented tasks.

Treatment can be given wherever a computer is available, e.g., home, school or clinic, and non-medical personnel can monitor the session.

In general, in one aspect, the invention features a method for treating visual dysfunctions, such as amblyopia, including steps of providing an interactive visual game that presents to the patient a visual task, the visual game employing images scaled to the patient's threshold for a visual parameter, and presenting a nonvisual reward to the patient for successful completion of the task.

Preferably, for treatment of amblyopia, the better eye is occluded while the visual task is presented to the amblyopic eye.

The images displayed to each patient are selected by the therapist by inputting age, IQ, and any preferences to hold that particular patient's attention throughout the therapeutic session and are selected according to that particular patient's visual capabilities. Visual images presenting tasks for the patient's interaction can include, for example, cartoon characters, including cartoon "personalities" popular with the patient's age group. Preferably a large number of various images are available for presentation, either in selected sequence or at random, so that the patient does not become bored by repetition; the images can vary in background pattern or color, and in outline form or color of a figure, as well as in the presentation of the task. Most preferably a large number of forms, patterns, and shades of color can be presented.

Preferably, the auditory reward is a sound pleasing to the patient, and more preferably the auditory reward includes a musical selection such as a song, chosen by the particular patient or selected from a group of musical selections chosen by the patient.

Preferably, the results of the subject's interactions are recorded during or following each treatment session, so that all parameters can be monitored and adjusted for each subject as the therapy progresses. More preferably, the information processor records the interactions in real time, and most preferably the information processor automatically adjusts the parameters in real time during the treatment session.

In general, in another aspect, the invention features apparatus for testing and treating visual dysfunctions, such as amblyopia in a patient, including means for presenting an image to the patient, the image presenting a visual task to the patient, means for automatic scaling in real time the image to about the patient's threshold value for a visual parameter previously determined from testing, means for providing an interaction between the patient and the image, and means for providing a reward for successful completion of the task.

Preferably, the means for providing for interaction between the patient and the image includes input means operable by the patient, and data processing means operatively connected to the input means and the image presenting means; the image presenting means includes a video monitor; and the input means includes a keyboard.

In general, in another aspect, the invention features an interactive video apparatus, including video display means for simultaneously stimulating a subject's interest and stimulating the subject's vision at about the maximum of each visual parameter of which the subject is capable, means for receiving input from the subject, and means for providing to the subject a nonvisual reward for subject input that is appropriate to an image presented to the subject on the video display means.

In preferred embodiments the display means is a video monitor, preferably a color video monitor, more preferably a high resolution video monitor, and more preferably a color video monitor capable of displaying a large number of shades of color (e.g., 365 shades of color).

The invention, in another aspect, features a method for testing a series of visual parameters of a patient, in particular crowding phenomenon, contrast sensitivity, color, brightness, pattern, stereopsis, flicker, motion and binocularity. The method comprises providing an interactive visual test that presents to the patient a random orientation of one or more letter E's and, in step increments, determines the patient's threshold value for the visual parameter with means for providing for interaction between the patient and the image.

DESCRIPTION OF PREFERRED EMBODIMENTS

Drawings

Figure 1:
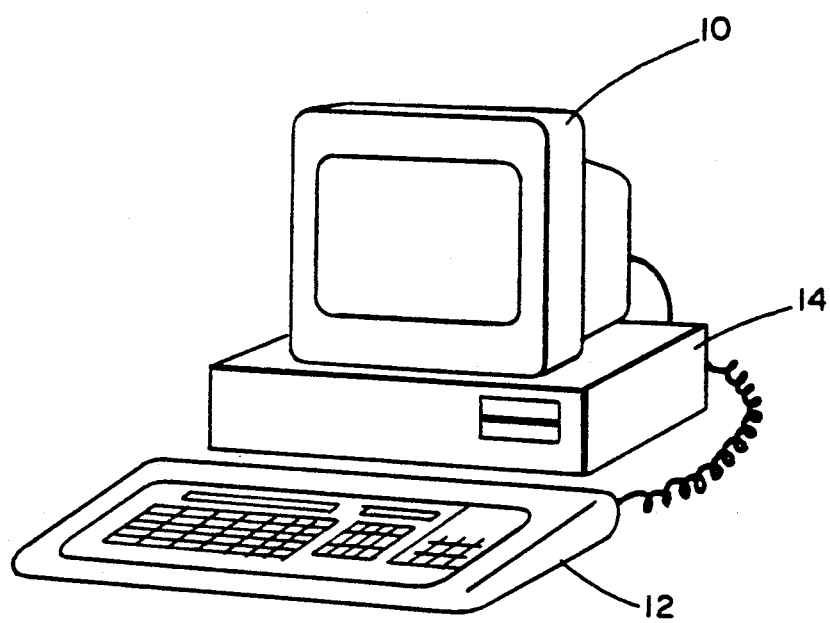

FIG. 1 is a diagram in perspective view showing apparatus according to the invention.

Structure

With reference to FIG. 1, apparatus according to the invention includes video display 10 for presenting images to a subject, keyboard 12 by which the subject provides input to the apparatus, and data processor 14 interactive with computer programs, including software, for generating the images presented on video display 10, for evaluating the patient's responses as provided by keyboard 12, and for recording the patient's responses as the treatment session progresses.

The description that follows details, by way of example, information processing steps carried out by the data processor for a selection of tasks ("games") that can be carried out by the patient during a treatment session. It will be appreciated that the particular tasks described in these examples can be carried out by information processing steps different from those shown in these examples; and that other tasks can be presented, all within the spirit and scope of the invention as a whole.

In general, the examples employ a set of "picture files", in which images and their variations are created and stored. Generally for each patient and for each treatment session, the person supervising the treatment session, who may be a trained therapist or a person acting on the instructions of a trained therapist, begins by setting up files particularly tailored to the particular patient's needs. Files are set up for providing background data regarding the patient's clinical presentation; for testing and recording various visual capability parameters for the patient; for selecting the task to be presented to the patient i.e., the game to be played by the patient) and the backgrounds on which the images are to be presented; for determining parameters of the level of challenge of the tasks (e.g., time allotted for the patient's response; rate at which the difficulty of the task is changed); for selecting the length of duration of the session; and for selecting the nonvisual (e.g., auditory) reward for a successful interaction.

Format of the picture files (For all games except Stereopsis Game)

All pictures ("P") are entered through a scanner or created and stored in any other fashion in an outline format. Each picture is assigned to a file corresponding to [a] particular age group[s] ("x"), depending on the complexity of the picture. Each enclosed area in the picture is assigned a number. These numbers can then be used to create a look up table of many possible color combinations for this picture ("C").

Variations of picture P are then created, either by entering them through the scanner or creating them on the screen. These variations ("V") are stored in a file "PV". Those pictures whose variations on the original picture P consist of differences in the contour are stored in a subfile called "PVcon".

Format of the picture files for Stereopsis Game

All pictures ("SP") are generated according to the formulas using Random Dot Steregrams ("RDS"), originally described by Bela Julesz, AT&T Bell Laboratories, N.J., (1960). The Same Pictures ("SP") are then generated in one Dimensional Black Outlines, creating a file "SP1D".

In these examples, the person supervising the treatment session begins by setting up the patient's files on a "Main Menu", as follows.

MAIN MENU (1) New Patient Data Input
(2) Test visual acuity ("VA")
(3) Test Crowding Phenomenon ("CPP")
(4) Test Contrast Sensitivity ("CSF")
(5) Test Binocularity ("BIF")
(6) Test Stereopsis ("STF")
(7) Select game to be played
(8) Select background
(9) Select the LIMIT (% correctly answered tasks, before the difficulty of the task is increased)
(10) Set N (the number of choices per task)
(11) Select INCREMENT (% of difficulty increase)
(12) Set TIME (maximum time allotted per task)
(13) Select TUNE
(14) Set GAME TIME (time of each game session in minutes)
(15) Display all parameters from previous session with ability to retain any number of them.

If (1) is selected from the Main Menu, the following data are input:
(a) Patient's name
(b) Age
(c) Clinical data If (2) is selected:
(a) Present random orientation of capital letter E (start with the largest).
(b) If the patient selects correct key (corresponding to the presented orientation of the letter) reduce the size of the next presented letter by 10%.
(c) If incorrect answer given, present the letter in the same size again.
(d) If three consecutive incorrect answers are given, to to (e), otherwise return to (c).
(e) Increase the size of the next presented letter E by 2%.
(f) If three consecutive correct answers are given, the size of the capital letter E correlates to the Visual Acuity (VA).
(g) If the number of correct answers is less than three, go back to step (e).

If (3) is selected:
(a) Present 4 capital letter E's, all in the same randomly determined orientation (beginning with the largest size and the largest spacing between the letters).
(b) If the patient selects the correct key (corresponding to the presented orientation of the letters) reduce the size of the letters by 5%, and present the row in a new randomly determined orientation.
(c) If the patient makes an incorrect response, present the row of letters at the same size and spacing in a new randomly determined orientation.
(d) If the patient selects the correct key (corresponding to the presented orientation of the letters) reduce the spacing between the letters by 5%, and present the row again in a new randomly determined orientation.
(e) If the patient makes an incorrect answer, present the letters with the same spacing in a new randomly determined orientation.
(f) If the patient makes three consecutive incorrect the size of the capital letters E and the distance between them correspond to the parameters of the Crowding Phenomenon ("CPP") for the patient.
(g) If the number of incorrect answers is less than three, go back to step (3)(b).

If (4) is selected:
(a) Ask the operator to select F1 and F1 which represent lower and upper limit of frequency range to be tested.
(b) Ask the operator to delect dF, i.e. desired steps of increment of frequency.
(c) Ask the operator to select dC, i.e. desired steps of reduction in contrast of the letter and its background.
(d) Let frequency F=F1.

(e) At frequency F, present random orientation of capital letter E (start with the strongest contrast between the background and the letter E).

(f) If the patient selects correct key (corresponding to the presented orientation of the letter) reduce the contrast of the next presented letter and its background by dC.

(g) If incorrect answer given, present the letter of the same contrast again.

(h) If three consecutive incorrect answers are given, the contrast correlates to the Contrast Sensitivity Function (CSF) value at F.

(i) If the number of incorrect answers is less than three, go back to step (e).

(j) If $F<F2$, increment F by dF and go to (e), otherwise store $CSF(F1-F2)$.

(k) Ask if printout of CSF is wanted, and in what format, i.e. tabulated values or a plotted graph.

If (5) is selected:

(a) Direct the patient to put on the Red/Green Glasses.

(b) Present a capital letter E (beginning with the largest size) in randomly determined orientation with one vertical line in each orientation being green and the other three lines being red.

(c) If the patient selects the correct key (corresponding to the presented orientation of the letter) go to step (5)(d), otherwise repeat step (5)(b).

(d) Present a capital letter E (in the same size as in step (5)(b)) in randomly determined orientation with one vertical line in each orientation being red and the other three lines being green.

(c) If the patient selects the correct key (corresponding to the presented orientation of the letter), reduce the size of the letter by 5%, and present the letter again in a new randomly determined orientation.

(d) If the patient makes an incorrect response, present the letter in the same size in a new randomly determined orientation.

(d) If the patient makes three consecutive incorrect responses, the size of the presented capital letter E correlates to the binocularity factor "BIF" for the patient.

(e) If the number of incorrect answers is less than three, go back to step (5)(b).

If (6) is selected:

(a) Ask the operator to select dSTF=incremental step of stereopsis difficulty.

(b) Direct the patient to put on the Red/Green Glasses.

(c) Present a capital letter E in randomly determined orientation using Random-Dot Stereograms (beginning with the least stereopsis difficulty).

(d) If the patient selects the correct key (corresponding to the presented orientation of the letter), reduce the stereopsis difficulty by dSTF, and present the letter in a new randomly determined orientation.

(e) If the patient makes an incorrect response, present the letter at the same stereopsis difficulty in a new randomly determined orientation.

(f) If the patient makes three consecutive incorrect responses, the degree of stereopsis correlates to the factor "STF" for the patient.

(g) If the number of incorrect answers is less than three, go back to step (6)(c).

If (7) is selected: Present Game Menu.

If (8) is selected: Present Background Menu.

If (13) is selected: Present TUNE Menu.

Then the person supervising the treatment session selects one or more tasks to be presented (games to be played) from a "Game Menu". These choices can also be preprogrammed by the physician for a whole series of therapy sessions. The game menu presents tasks designed to challenge and exercise in various ways particular visual capabilities of the patient during the treatment session. Such games can include, by way of example, the following.

GAME MENU (1) Identify Game (for moving target set speed)
   (a) VA only with moving target
   (b) VA only with stationary target
   (c) CPP only with stationary target
   (d) CPP only with moving target
   (e) CSF only with moving target
   (f) CSF only with stationary target
   (g) VA and CSF with stationary target
   (h) VA and CSF with moving target
   (i) CPP and CSF with moving target
   (k) CPP and CSF with stationary target (2) Different Game (allow selection for target movement as in Identify Game (1)
   (a) VA only
   (b) CSF only
   (c) CPP only
   (d) VA and CSF
   (e) CPP and CSF (3) Match Game (allow selection for target movement as in Identify Game (1)
   (a) VA only
   (b) CSF only
   (c) VA and CSF (4) Shadow Game (allow selection for target movement as in Identify Game (1)
   (a) VA only
   (b) CSF only
   (c) VA and CSF (5) Binocular Game (allow selection for target movement as in Identify Game (1)

(6) Stereopsis Game (allow selection for target movement as in Identify Game (1)

BACKGROUND MENU

Select the desired combination:

(1) Solids
(2) Checkerboard
   (a) set moving speed
   (b) set limit on the square size (function of VA)
   (c) choose contrast (using CSF)
(3) Stripes
   (a) set moving speed
   (b) set limit on the width
   (c) choose contrast
   (d) choose angle and arc
(4) Dots
   (a) set moving speed
   (b) set limit on the diameter
   (c) choose contrast
   (d) select random vs. patterned
(5) Target and Answer background
   (a) same
   (b) different (repeat choices 1-4)

The person supervising the treatment session selects, according to the preference of the patient, an auditory reward by using a "Tune Menu", for example as follows.

TUNE MENU (1) Tune throughout therapy
  (a) same each session
  (b) change each session
(2) Present for the patient's selection a list of 8 names of children's songs with corresponding numbers, with the option of hearing each tune.
(3) Select the TUNE which will be the reward tune for correct answers.

By way of example, processing steps for presenting each of the games listed in the "Game Menu", described above, can be as follows.

IDENTIFY GAME

(10) Select picture file (X) according to age.
(20) If GAME TIME has been exceeded, END game and save all parameters, ELSE continue.
(25) Select random picture (P) from this file.
(30) Select random color combination from file of P ("PC1").
(40) If VA function was selected, scale P according to VA. Plot scaled picture (PC1s).
(50) If CPP function was selected, scale P according to CPP. Plot a number of scaled, colored pictures in a row.
(60) From file X select (N−1) pictures randomly.
(70) Select random color combinations for each of (N−1) pictures.
(80) Plot in the original (large) size PC1 and (N−1) Pictures.
(90) If CSF function was selected, choose background using CSF values and background parameters selected earlier.
(100) If CSF was not selected, choose background using only background parameters.
(110) If target and background were selected to be the same, plot the background on the whole screen; otherwise plot the selected background in the square around the scaled picture. Select background2 using background parameters and plot it on the rest of the screen.
(120) Ask the patient to find the same picture as PC1s from among the choices.
(130) If PC1 is selected, sound the chosen TUNE and increment the counter of correct answers by 1.
(140) If picture selected is different than PC1, buzz is sounded.
(150) If no selection is made in TIME allotted, buzz is sounded.
(160) Increment the counter of total pictures presented by 1.
(170) If # correct/total # does not equal LIMIT go to (20), else continue.
(180) Change VA, CPP, CSF by INCREMENT.
(190) Go to (20).

DIFFERENT GAME

(10) Select picture file (X) according to age.
(20) If GAME TIME has been exceeded, END game and save all parameters, ELSE continue.
(25) Select a picture ("P") at random from this file.
(28) Select a random variation ("PV") of picture P.
(30) Select a random color combination ("PC1") of P.
(40) If VA function was selected, scale P and PV according to VA.
(50) If CPP function was selected, scale according to CPP.
(60) Plot N scaled copies of P and one scaled copy of PV: randomly on the screen if VA chosen, or in a row if CPP chosen.
(90) If CSF function was selected, choose background using CSF values and background parameters selected earlier.
(100) If CSF was not selected, choose background using only background parameters.
(110) If target and background were selected to be the same, plot the background on the whole screen; otherwise plot the selected background in the square around the scaled picture. Select background2 using background parameters and plot it on the rest of the screen.
(120) Ask the patient to find among the pictures the one that is different from the others.
(130) If PV is selected, sound the chosen TUNE and increment the counter of correct answers by 1.
(140) If picture selected is different than PV, buzz is sounded.
(150) If no selection is made in TIME allotted, buzz is sounded.
(160) Increment the counter of total pictures presented by 1.
(170) If # correct/total # does not equal LIMIT go to (20), else continue.
(180) Change VA, CPP, CSF by INCREMENT.
(190) Go to (20).

MATCH GAME

(10) Select picture file (X) according to age.
(20) If GAME TIME has been exceeded, END game and save all parameters, ELSE continue.
(25) Select random picture (P) from this file.
(28) Select (N−1) random pictures from file PV (all are variations of the original picture P).
(30) Select random color combination from file of P ("PC1").
(40) If VA function was selected, scale P and PV(N−1) according to VA.
(60) Plot scaled copy of P in a box. Plot another scaled copy of P and scaled PV(N−1) randomly on the screen.
(90) If CSF function was selected, choose background using CSF values and background parameters selected earlier.
(100) If CSF was not selected, choose background using only background parameters.
(110) If target and background were selected to be the same, plot the background on the whole screen; otherwise plot the selected background in the square around the scaled picture. Select background2 using background parameters and plot it on the rest of the screen.
(120) Ask the patient to find among the pictures the one that is the same as the one in the box.
(130) If P is selected, sound the chosen TUNE and increment the counter of correct answers by 1.
(140) If picture selected is other than P, buzz is sounded.
(150) If no selection is made in TIME allotted, buzz is sounded.
(160) Increment the counter of total pictures presented by 1.

(170) If # correct/total # does not equal LIMIT go to (20), else continue.
(180) Change VA, CSF by INCREMENT.
(190) Go to (20).

SHADOW GAME

(10) Select picture file (X) according to age.
(20) If GAME TIME has been exceeded, END game and save all parameters, ELSE continue.
(25) Select random picture (P) from this file.
(30) Select color combination from file of P (PC1) where all areas are the same color (i.e., only the outline can be distinguished).
(40) From file PVcon select (N−1) pictures at random.
(50) If VA function was selected, scale P and PVcon(N−1) according to VA.
(70) Select random color combination from file of P (PC2).
(80) Plot scaled PC1 in the box. Plot randomly on the screen, PC2 and PVcon(N−1) in C2 color combination.
(90) If CSF function was selected, choose background using CSF values and background parameters selected earlier.
(100) If CSF was not selected, choose background using only background parameters.
(110) If target and background were selected to be the same, plot the background on the whole screen; otherwise plot the selected background in the square around the scaled picture. Select background2 using background parameters and plot it on the rest of the screen.
(120) Ask the patient to find the same picture as PC1 in the box.
(130) If PC2 is selected, sound the chosen TUNE and increment the counter of correct answers by 1.
(140) If picture selected is other than PC2, buzz is sounded.
(150) If no selection is made in TIME allotted, buzz is sounded.
(160) Increment the counter of total pictures presented by 1.
(170) If # correct/total # does not equal LIMIT go to (20), else continue.
(180) Change VA, CSF by INCREMENT.
(190) Go to (20).

The following game is designed for improvement of fusion.

BINOCULAR GAME

(10) Select picture file (X) according to age.
(20) If GAME TIME has been exceeded, END game and save all parameters, ELSE continue.
(25) Select random picture (P) from this file.
(30) Scale P according to BIF (Ps).
(40) Select RED/GREEN color combination from file of P (PC1).
(50) Plot scaled RED/GREEN picture (PC1s) in the box.
(60) Plot Ps with all RED=WHITE and all GREEN=BLACK ("PW/B").
(70) Plot Ps with all RED=BLACK and all GREEN=Background.
(75) Plot Ps with all GREEN=Black and all RED=Background.
(80) Select random (N−3) pictures from PVcon.
(85) Scale PVcon(N−3) pictures according to BIF.
(90) Plot scaled PVcon(N−3) pictures in Black/White colors.
(120) Ask the patient to find the same picture as RED/GREEN Ps in the box.
(130) If PW/B is selected, sound the chosen TUNE and increment the counter of correct answers by 1.
(140) If picture selected is other than PW/B, buzz is sounded.
(150) If no selection is made in TIME allotted, buzz is sounded.
(160) Increment the counter of total pictures presented by 1.
(170) if # correct/total # does not equal LIMIT go to (20), else continue.
(180) Change BIF by INCREMENT.
(190) Go to (20).

The following game is designed for improvement of stereopsis.

STEREOPSIS GAME

(20) If GAME TIME has been exceeded, END game and save all parameters, ELSE continue.
(25) Select picture x at random from file SP.
(40) Scale SPx according to STF.
(50) Plot scaled picture.
(60) Select and plot the same picture x from SP1D, i.e., the same picture but in one dimension.
(70) From file SP1D randomly select and plot (N−1) pictures.
(80) Ask the patient to find the same picture as SPx from among the choices.
(130) If SP1Dx is selected, sound the chosen TUNE and increment the counter of correct answers by 1.
(140) If picture selected is other than SP1Dx, buzz is sounded.
(150) If no selection is made in TIME allotted, buzz is sounded.
(160) Increment the counter of total pictures presented by 1.
(170) if # correct/total # does not equal LIMIT go to (20), else continue.
(180) Change STF by INCREMENT.
(190) Go to (20).

Use

The method of the invention can be used for treatment of amblyopia in children or in adults at any age (>2.5 years) or cognitive level, by setting up the files to suitably tailor the challenges presented by the games and the reward for successful interactions to the needs and preferences of the individual patient.

Typically, a therapeutic regimen using the invention may include, for a patient 7 years old, a series of 4 treatments per week, each of 30 minutes duration, over a period of 4 weeks to 6 months, depending on the visual acuity at the onset of therapy and rate of improvement for that particular individual.

The invention provides, by selection of any of various tasks, for treatment not only of visual acuity deficiencies, but of any of the defects of amblyopia, including, for example, defects of contrast sensitivity, crowding phenomenon, binocularity, and stereopsis.

Apparatus according to the invention provides a complete therapy unit, capable of use in testing, treating, and monitoring and analyzing each patient's progress. The invention provides for a therapeutic regimen tailored by the therapist for the individual patient's needs, and continual real time monitoring of progress and automatic adjustment of the tasks to keep the level of challenge at about the patient's capability level.

Other eye conditions than amblyopia are characterized by one or more of the deficiencies that are tested and exercised according to the invention; and the invention can be used to determine the status or monitor the progression of any of these other conditions. For example, the contrast sensitivity test can be used in monitoring the progression of glaucoma (or in following the progress of treatment).

Visual parameters that can be tested using the invention include visual acuity, crowding phenomenon, contrast sensitivity, color, brightness, pattern, stereopsis, flicker, motion, and binocularity. The invention can be used in conjunction with other methods to assess involvement of neurovisual pathways in patients with defects of higher visual processing.

The games can be used as a general educational aid, as for example in "intelligence training" in preschool and school age children having mild mental retardation.

Other Embodiments

Other embodiments are within the following claims. For example, the hardware can be a free standing self-contained unit, capable of performing any or all the functions described. The hardware can be portable. The software containing the processing steps can be adapted for use with any computer terminal, including, for example, a home personal computer. Standard keyboards can be readily adapted for particular input; for example, specified keys can be set up for input of a test using tumbling capital E.

Separate software packages can be provided for any of the visual parameters, together with programs for storing, comparing, and analyzing the data from each interaction or treatment session.

We claim:

1. A method for testing and treating visual dysfunctions in a patient, comprising determining a threshold value for the patient's visual parameter or parameters, providing an interactive visual game that presents to the patient a visual task, said visual game employing an image or images selected as suited to the patient's interest and scaled to the patient's determined threshold value for the visual parameter or parameters, and presenting a non-visual reward to the patient for successful completion of the task.

2. The method of claim 1 wherein said visual dysfunction is amblyopia.

3. The method of claim 2 further comprising occluding the patient's better eye, whereby the visual task is presented only to the amblyopic eye.

4. The method of claim 1 or 2 wherein a variety of images comprising a variety of forms, patterns, and shades of color are available for presentation to the patient.

5. The method of claim 1 or 2 wherein said reward comprises a sound pleasing to the patient.

6. The method of claim 1 or 2 wherein said reward comprises a musical selection chosen by the patient or selected from a group of musical selections chosen by the patient.

7. The method of claims 1 or 2 further comprising recording results of the patient's interactions with said visual game during or following each treatment session, and adjusting the scaling of said images in response to changes in the patient's threshold value for a visual parameter or parameters as therapy progresses.

8. The method of claims 1 or 2 further comprising monitoring the patient's interactions with said visual game in real time during each treatment session, and adjusting the scaling of said images in response to changes in the patient's threshold value for a visual parameter or parameters in real time during a treatment session.

* * * * *